United States Patent

Diekmann et al.

[11] Patent Number: 5,377,526
[45] Date of Patent: Jan. 3, 1995

[54] TRACTION ANALYZER

[75] Inventors: Bruno Diekmann, Sturtevant, Wis.; Lawrence H. Dubé, Zion, Ill.

[73] Assignee: Racine Flame Spray Inc., Racine, Wis.

[21] Appl. No.: 148,023

[22] Filed: Nov. 4, 1993

Related U.S. Application Data

[63] Continuation-in-part of Ser. No. 939,792, Sep. 3, 1992, abandoned.

[51] Int. Cl.$^6$ ............................................. G01N 19/02
[52] U.S. Cl. ................................................................. 73/9
[58] Field of Search ................................ 73/7, 9, 10

[56] References Cited

U.S. PATENT DOCUMENTS

| | | | |
|---|---|---|---|
| 2,225,140 | 12/1940 | Walker | 73/9 |
| 3,020,744 | 2/1962 | Long | 73/9 |
| 3,098,377 | 7/1963 | Beauchamp | 73/9 |
| 4,120,191 | 10/1978 | Fly et al. | 73/9 |
| 4,197,902 | 4/1980 | Von Jan et al. | 164/72 |
| 4,682,418 | 7/1987 | Tuss et al. | 33/1 M |
| 4,813,266 | 3/1989 | Nash | 73/9 |

Primary Examiner—Robert Raevis
Attorney, Agent, or Firm—Wheeler & Kromholz

[57] ABSTRACT

An apparatus for measuring the coefficient of friction between a strip of paper and a surface finishable by flame spraying, comprising a weight pressing on an interface between the paper and the flame sprayed workpiece, a force measuring means attached to the paper, and a constant speed motor that moves the paper past the interface point. The weight with mass exerts a known force upon the surfaces. The force measuring means is attached to the paper between the interface and the motor. The paper attached to the force measuring means is drawn past the interface by the motor at constant speed as the force measuring means measures the force. The measurement allows such surfaces to be compared and evaluated.

5 Claims, 5 Drawing Sheets

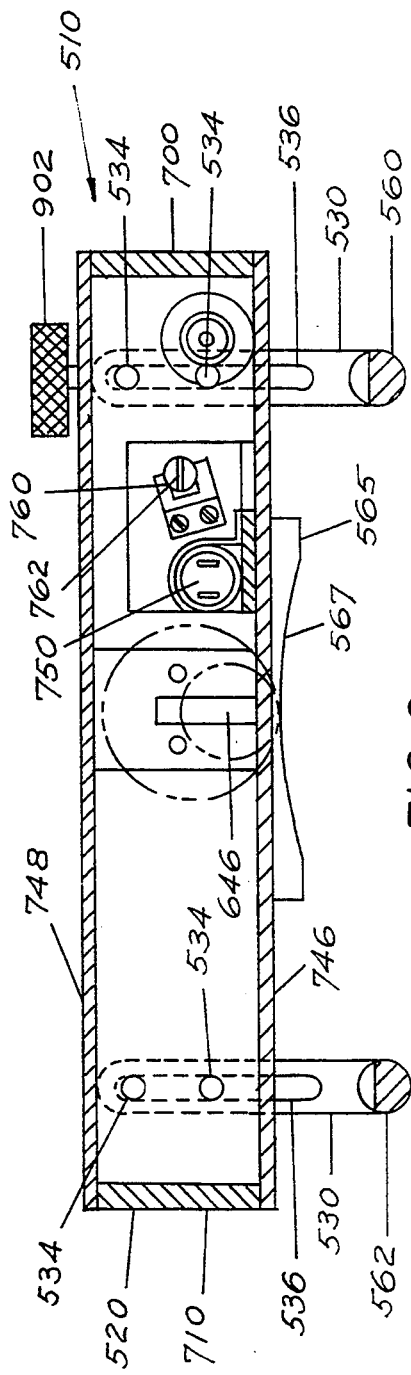
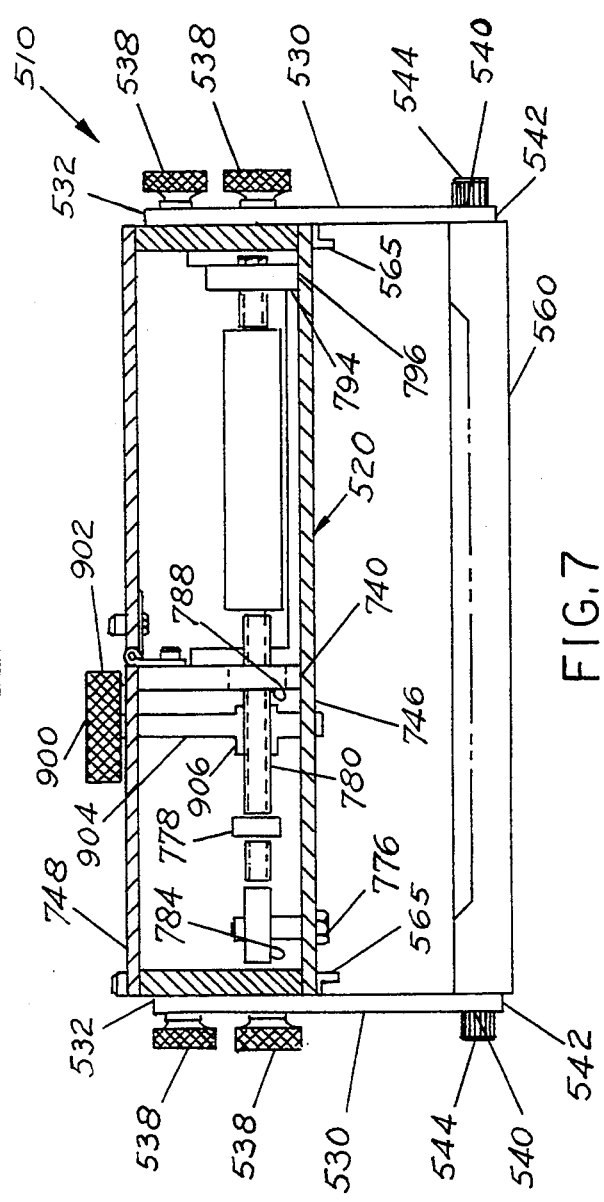

TRACTION ANALYZER

This application is a continuation-in-part, of application Ser. No. 07/939,792 filed Sep. 3, 1992, now abandoned.

BACKGROUND OF THE INVENTION

It is often necessary to apply a frictional coating to the surface of a machine's feeding or dispensing mechanisms that contact the material fed into or discharged from the machine. The frictional surface must have a coefficient of friction high enough to enable each mechanism to properly grip and guide the material but not so high as to damage the material. The coated surface wears away over a period of use to the point where its reduced coefficient of friction no longer permits proper feeding or dispensing. If the material is abrasive, as paper is, the wear is increased. It then becomes necessary to rejuvenate the frictional surface to its original characteristics.

It is well known in the art that through the use of a flame spray process a frictional surface can be created on a new part or a worn frictional surface can be rejuvenated on an old part. Flame spraying is a metalizing process whereby a frictional surface is created by spraying droplets of the desired surface material onto a machine part's surface. This process can be repeatedly used on the same part to restore the frictional surface which wears away during its service life, but small differences in the finished surface make major differences in its operating characteristics, and no measuring system is known. The coatings may be pure metal or ceramics such as oxides, carbides or other hard surfaces, or alloys.

For example, rolls used in the paper industry on machines for rolling paper into the width and diameter desired by the customer are often coated with an abrasive material so that they can grip and maintain the correct amount of tension during the paper rolling process, without slipping or tearing. The coating prevents slippage of the paper web on the bed roll of the winder during the construction of the finished roll. A properly rolled paper roll is tightly wound so it will not telescope during shipment. However, paper is an abrasive material. Thus the frictional surface on the roll typically wears out after a period of use. So that the roll can be reused, a new frictional surface is applied by a flame spray process.

Our traction analyzer measures the frictional surface of the coated machine part after the droplets of surface material have been applied through the flame spray process. Through its use the required coefficient of friction and service life attained by applying a given coating under known conditions can be estimated, and preferred conditions for treatment of each feeding or dispensing mechanism can be determined. It is an objective of our invention to enable the measurement of a machine part's surface in order to establish uniformity in the flame spraying process and in defining recoating intervals for particular workpieces and customers. Another objective of our invention is to provide such a measuring device that produces consistent and accurate data representing the frictional qualities of the surface's coating. Such data may be used to determine when re-surfacing is needed, or to characterize the results of re-surfacing to verify that a prescribed frictional characteristic has been attained. On a surface with a known characteristic, unknown papers may be tested to qualify them as test paper strips. It is a further objective of the invention to provide such a measuring device that is portable, compact, and easy to use.

SUMMARY OF THE INVENTION

Our invention has two embodiments. The first comprises a stationary base with long and short pairs of support arms having magnetic carriers to removably attach our traction analyzer to a curved frictional surface, typically a paper machine roll. The support arms allow the invention to remain in the selected position when attached to paper rolls of differing diameters. While this disclosure of our traction analyzer has been adopted for use on paper rolls, it can be utilized to determine the coefficient of friction of any surface, curved or flat. Other attachment means may be used for non-magnetic surfaces and for attachment to other objects.

Within the stationary base is housed a reversible electric motor whose output is connected to a traversing lead screw. The lead screw is threadedly attached to a traversing table. The traversing table rests on two bearing surfaces slightly above the top edge of the stationary base and is guided by two elongated guides. A force measuring instrument is attached to the top surface of the traversing table. A pair of pressure roller support arms are attached to the stationary base near the shorter pair of support arms. A shaft passes through the holes in the opposite ends of each roller support arm and through a hole in the central axis of the pressure roller. Thus the pressure roller, which has mass, rotates freely on the shaft between the roller support arms.

A long rectangular piece of test strip material, typically paper, with known or measured frictional characteristics is attached to the sensing input of the force measuring instrument and is threaded under the pressure roller such that the paper strip is positioned between the pressure roller and the workpiece paper roll having a frictional surface from the flame spray process to be evaluated. When the constant velocity reversible motor is engaged in the forward direction, it pulls the strip of paper between the roller and paper roll. Because the pressure roller has mass that exerts a known force upon the paper strip and the paper roll, a specific amount of force that varies with the frictional characteristics of the workpiece surface is required to overcome friction to pull the paper strip between the two structures. This force is transmitted to the sensing input of the force measuring instrument as the paper strip is pulled forward by the constant velocity motor. A limit switch stops the motor and traversing table automatically when it has traveled its full distance. The output of the force measuring instrument is directly proportional to the coefficient of friction of the paper roll's surface and can be subsequently converted into a value which has meaning to express the surface friction of the measured surface as a single number.

After the force measuring instrument's output has been recorded, the motor is reversed and the traversing table is returned to its original position. A second limit switch automatically stops the traversing table when it has indexed to its initial starting position. A new strip of paper, whose fibers have not been disrupted by the frictional surface of the paper roll, can now be attached to the force measuring instrument and threaded between the pressure roller and paper roll for the next measurement.

The second embodiment of our invention comprises a self contained unit in which the traversing table is replaced with a take up spool contained within the stationary base. The pressure roller and force measuring instrument are also contained within the stationary base.

The stationary base again desirably has two pairs of support arms to removably attach the traction analyzer to the curved surfaces of paper rolls of varying diameters. A support bar extends between each pair of support arms and rests on the paper roll's curved surface. As in the first embodiment, other attaching means may be used. Alternatively, two mounting brackets are attached on opposite sides on the bottom of the stationary base. Each bracket has a recessed portion which receives the curved surface of the paper roll. The predetermined radius of the recessed portion allows the stationary base to be placed on paper rolls of varying diameters.

A force measuring instrument, an impulse shaft, a pressure roller, a drive unit, a take up spool, and a power supply are contained within the base. The impulse shaft, functioning as a third class lever, extends from a pivot bearing to an end support bearing. The pivot bearing acts as the fulcrum point. The impulse shaft passes through the sensing input of the force measuring instrument and contains a roller near its opposite end. An end support bearing on its opposite end allows the impulse shaft to move around the fulcrum.

A strip of test material, typically paper, with known characteristics or measured characteristics, used to analyze the frictional characteristics of the paper roll, is threaded into the take up spool. The strip passes over and around the impulse shaft roller, through an opening in the bottom of the base, between the pressure roller and the paper roll to be analyzed, and over the rear support bar. The take up spool is driven by a constant velocity electric motor connected by two sheaves and a belt.

As disclosed in the first embodiment, the pressure roller has mass that exerts a known constant force on the paper test strip whose surface is in contact with the frictional surface of the paper roll. As the take up spool pulls the paper test strip between the pressure roller and paper roll, the required pulling force is transmitted to the roller end of the impulse shaft by the strip of paper which is wrapped around it. The impulse shaft end support bearing allows the shaft to move about the pivot bearing or fulcrum on the opposite end, thus acting as a third class lever. The force exerted upon the impulse shaft is subsequently transmitted to the sensing input of the force measuring instrument. Again, the output of the force measuring instrument is directly proportional to the coefficient of friction of the paper roll's surface and this output can be converted into a value which has meaning to express the surface friction of the measured surface as a single number.

In applications where structures located above the paper roll prevent the placement of our traction analyzer on the top of the paper roll, our horizontal accessory device is employed. The device includes a force producing bell crank having a fulcrum, pressure roller, and counterweight. The counterweight, which hangs from one end of the bell crank, has a mass sufficient enough to exert a force in the horizontal direction equal to the gravitational force exerted by the pressure roller in the vertical direction. Using this device, it is possible to determine the coefficient of friction between the strip of paper and the paper roll from the side of the paper roll as opposed to the top. The test strip of paper passes between the horizontal accessory pressure roller and the surface of the paper roll and into the nearby located traction analyzer in the same manner as discussed above.

Thus after a paper roll's frictional surface has been worn away and is rejuvenated by a flame spray process, the coefficient of friction necessary for the paper roll to perform its proper function can be accurately achieved with the use of my traction analyzer. Furthermore the coefficient of friction of the paper roll can be checked during maintenance intervals so that the roll can be removed and recoated at the proper time.

DESCRIPTION OF THE DRAWINGS

FIG. 6 is a cross-sectional view of the second embodiment of the traction analyzer on line 6—6 of FIG. 5.

FIG. 7 is a cross-sectional view of the second embodiment of the traction analyzer on line 7—7 of FIG. 5.

FIG. 8 is a side view of the horizontal accessory device.

FIG. 9 is an end view of the horizontal accessory device.

FIG. 10 is a schematic side view showing the application of the horizontal accessory device to a paper roll.

DETAILED DESCRIPTION

Figure 1:
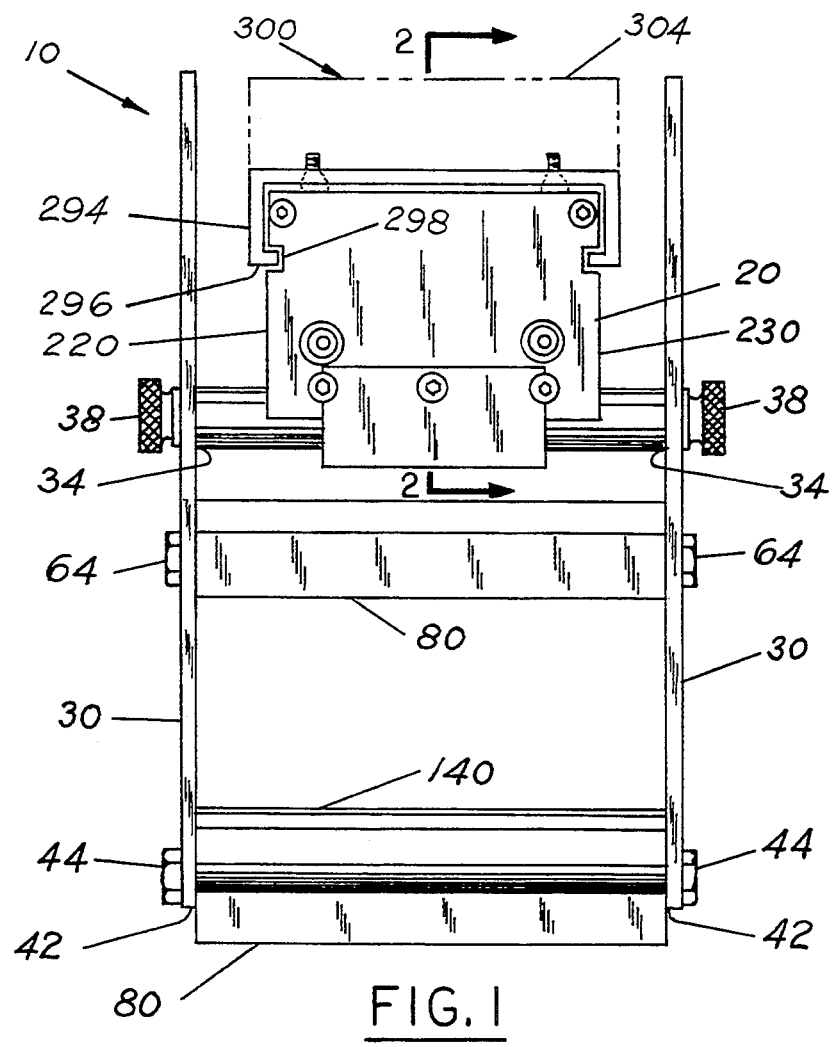
FIG. 1 is a front view of the first embodiment of the traction analyzer.
Figure 2:
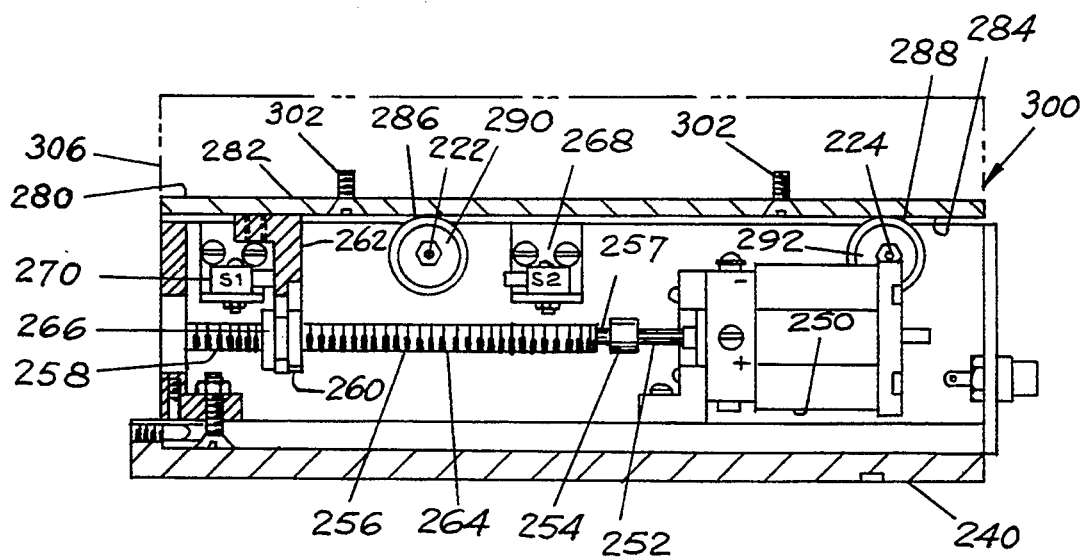
FIG. 2 is a cross-sectional view of the first embodiment of the traction analyzer taken on line 2—2 of FIG. 1.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The first embodiment of this traction analyzer will be referred to as 10 and is shown in FIGS. 1, 2, 3, and 4.

The traction analyzer of this embodiment has a stationary base 20 to which a pair of long support arms 30 and a pair of short support arms 50 are attached at 34 and 54 respectively. Each pair of support arms 30 and 50 have elongated slots 36 and 56 through which thumb screws 38 and 58 pass to hold pairs of support arms 30 and 50 in their desired positions. Each pair of support arms 30 and 50 also have apertures 40 and 60 located near their opposite ends 42 and 62. Fastening means 44 and 64 pass through apertures 40 and 60 and pivotally attach magnetic carriers 80 between pairs of support arms 30 and 50. Pivotal magnetic carriers 80 and elongated slots 36 and 56 allow stationary base 20 to be removably attached to a cylindrical frictional surface, typically a paper roll, of any diameter. Other attachment means may be used for non-magnetic surfaces and for attachment to other objects.

Roller support arms 100 are pivotally attached to stationary base 20 at point 70 by thumb screws 74. The opposite ends 102 of support arms 100 contain apertures 104. Shaft 142 passes through apertures 104 of roller support arms 100 and inner races 144 of bearings 146. The outer races 150 of bearings 146 are fixedly attached concentric to the central axis of pressure roller 140 by fastening means 154. Thus pressure roller 140 rotates freely on bearings 146 around shaft 142. To insure that the force exerted by the pressure roller 140 upon the cylindrical frictional surface is the same for each cylindrical frictional surface, the traction analyzer should be attached at the same location on each cylindrical frictional surface tested. Thus the force from the mass of the pressure roller 140 upon the tangential line of contact between pressure roller 140 and the cylindrical frictional surface is the same for each cylindrical frictional surface.

Stationary base 20 has a box-like structure with five walls: a front wall 200, a back wall 210, a right side wall 220, a left side wall 230, and a bottom wall 240. Contained within the box-like structure of stationary base 20 is constant velocity electric motor 250 with an output shaft 252. Coupling 254 connects output shaft 252 to end 257 of traversing lead screw 256. Traversing lead screw 256 is supported at its other end 258 by floating nut 260. Floating nut 260 is fixedly attached to traversing table 280 by bracket 262.

Traversing table 280 has a fiat, planar top surface 282 to which a strain gage or force measuring instrument 300 is removably attached by fastening means 302. The bottom surface 284 of traversing table 280 rests and traverses on bearing surfaces 286 and 288 of beatings 290 and 292 respectively. Beatings 290 and 292 are supported on and rotatably attached to side walls 220 and 230 of stationary base 20 at 222 and 224.

Traversing table 280 has two sides 294 which have lower inward protrusions 296. Inward protrusions 296 slidably engage into elongated slots 298 in side walls 220 and 230 of stationary base 20. Thus the motion of traversing table 280 is restricted to a single plane in only one direction and its opposite direction.

Figure 3:
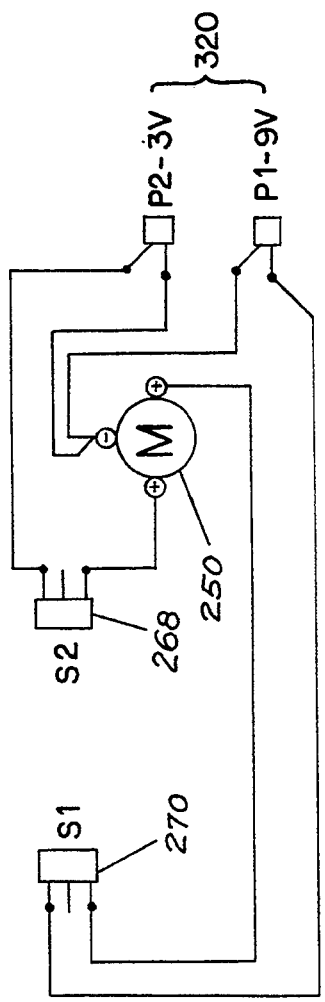
FIG. 3 is a schematic diagram of the circuit of the first embodiment.
Figure 4:
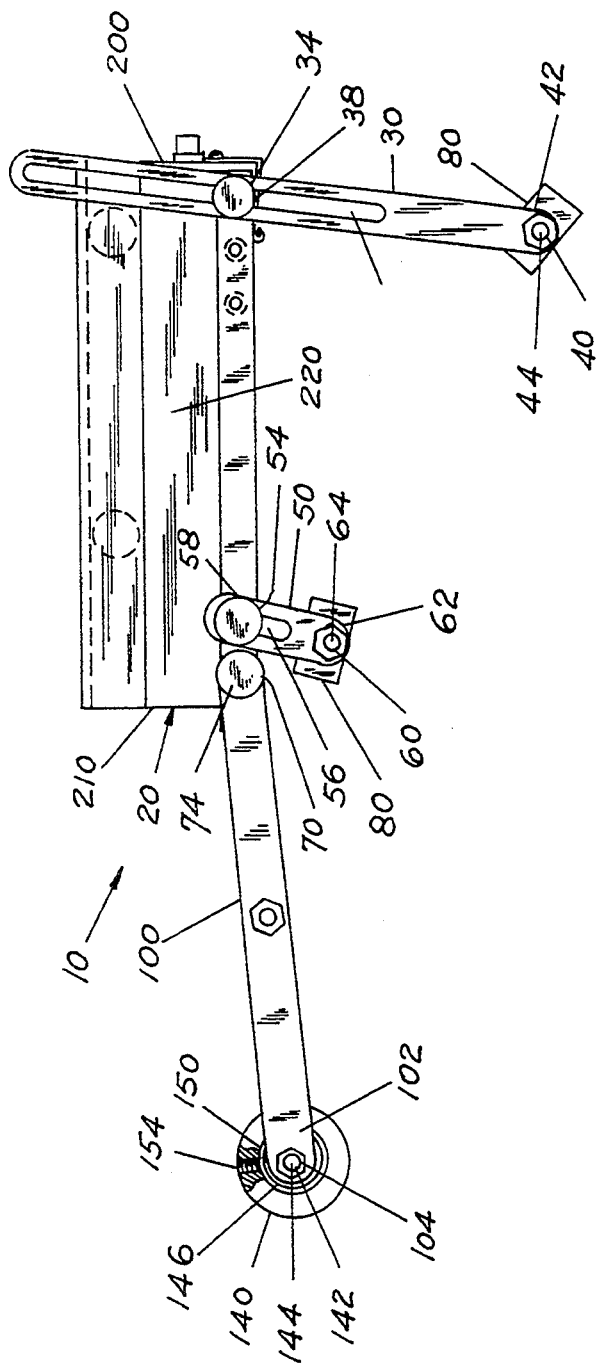
FIG. 4 is a right side view of the first embodiment of the traction analyzer.

When constant speed electric motor 250 is energized by power supply 320, output shaft 252, coupling 254, and traversing lead screw 256 rotate in a first rotational direction. The threads 264 of traversing lead screw 256 are threadedly engaged into the threads 266 of floating nut 260 which is fixedly attached to bracket 262. As traversing lead screw 256 continues to rotate, floating nut 260 advances along traversing lead screw 256. Because bracket 262 is fixedly attached to floating nut 260 and to traversing table 280, traversing table 280 moves at a constant velocity in its first direction. When bracket 262 contacts limit switch 268, the circuit shown in FIG. 3 is de-energized. When the polarity of the circuit is reversed, traversing lead screw 256 rotates in a second rotational or opposite direction and traversing table 280 travels in the opposite direction until bracket 262 contacts limit switch 270 which de-energizes the circuit. The traversing table 280 is now in its original position.

The end of a long, narrow, rectangular strip of paper is attached to the input sensor 306 of the strain gage or force measuring instrument 300. The strip is then placed beneath the pressure roller 140 and on top of the frictional surface or paper roll to be analyzed. As the constant velocity electric motor 250 is energized the traversing table 280 and force measuring instrument 300 move forward and pull the strip of paper between the pressure roller 140 and frictional surface interface. The force measuring instrument 300 records the force required to pull the paper strip. This force is displayed in a known way in the force measuring instrument's output 304, typically a digital read-out, and is recorded. The recorded pulling force is directly proportional to the coefficient of friction of the frictional surface analyzed. The force can be used directly or converted into a value which has meaning in the flame spray coating industry when compared with similar values measured on rolls with correct surface friction in the past, and when compared with values measured on worn rolls that lack proper frictional characteristics.

Figure 5:
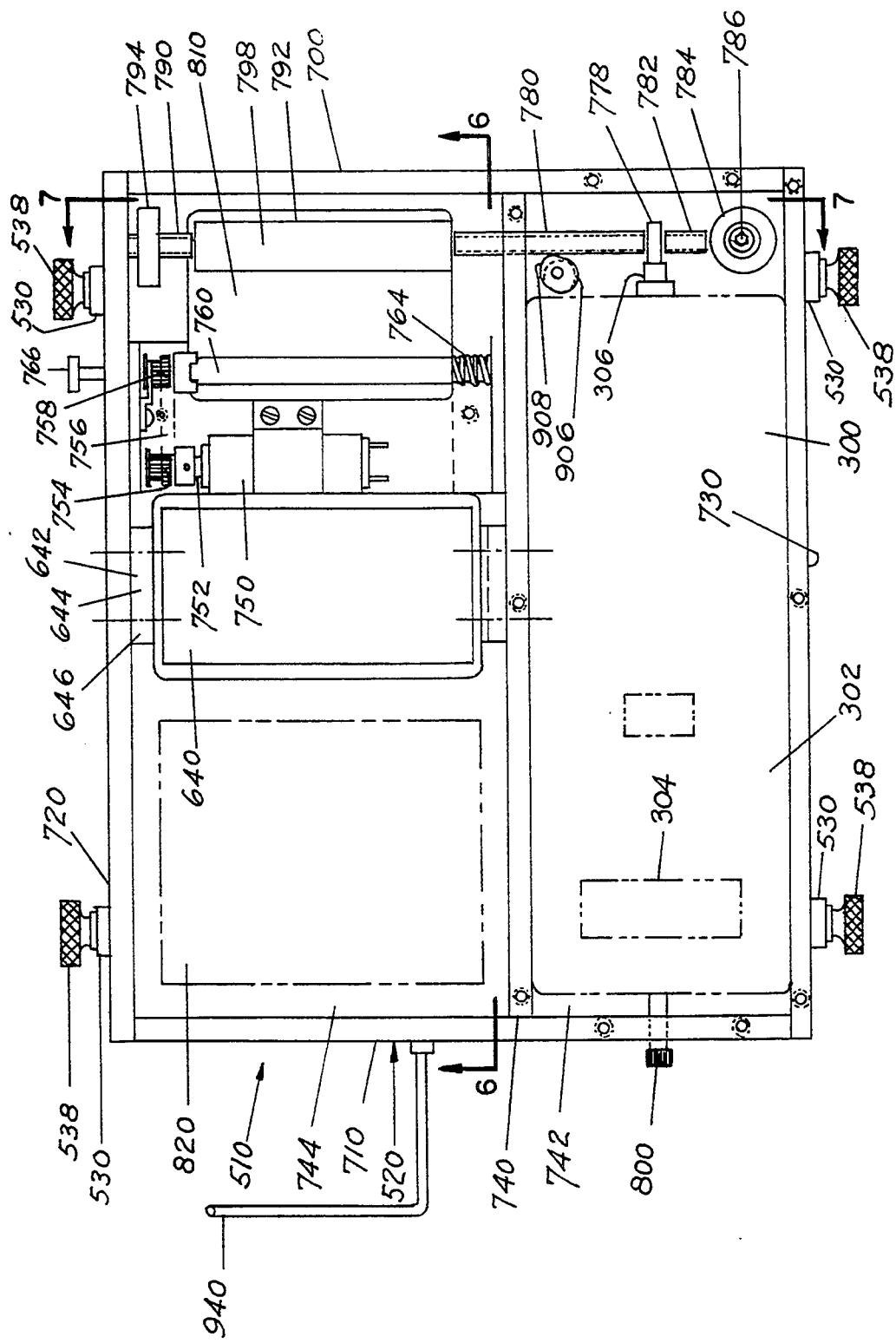
FIG. 5 is a top view of the second embodiment of the traction analyzer.

The second embodiment of the traction analyzer will be referred to as 510 and is shown in FIGS. 5 through 7.

The traction analyzer has a stationary base 520 to which the ends 532 of four support arms 530 are attached at 534. Each end 532 of each support arm 530 has an elongated slot 536 through which thumb screws 538 pass to hold support arms 530 in their desired position. The elongated slots 536 allow the stationary base 520 to be easily attached to a cylindrical structure, such as a paper roll, of any diameter. Each support arm 530 also has an aperture 540 located near its opposite end 542. Cap screws 544 pass through apertures 540 and rotatably attach front support bar 560 and rear support bar 562 between matching pairs of support arms 530. Alternatively, two mounting brackets 565 are attached to stationary base 520 as shown in FIGS. 6 and 7. The recessed portions 567 have a pre-determined radius which allows the traction analyzer 510 to be securely placed on paper rolls of varying diameters. Again, other attaching means may be used for attachment to different surfaces and objects. To insure that the force exerted by pressure roller 640 is the same for each cylindrical frictional surface, the traction analyzer should be attached in the same location on each cylindrical frictional surface tested. Thus the force from the mass of the pressure roller 640 upon the tangential line of contact between pressure roller 640 and the cylindrical frictional surface is the same for each cylindrical frictional surface.

Stationary base 520 has a box-like structure with six walls: a front wall 700, a back wall 710, a left side wall 720, a right side wall 730, a bottom wall 746 and a top wall 748. Additionally, a center wall 740 divides the box like structure of stationary base 520 into two interior cavities 742 and 744. Contained within cavity 744 of stationary base 520 is a constant velocity electric motor 750 with an output shaft 752. Electric motor 750 is powered by a power supply 820 also located in cavity 744. Sheave 754 is attached to output shaft 752 and drives belt 756 which in turn rotates sheave 758. Sheave 758 is attached to the end of take up spool 760. A narrow slot 762 passes through a portion of the central axis of take up spool 760 to facilitate the threading of the test strip material. The spool 760 is held in place by strip release spring 764 and can be released by pressing strip release pin 766. Depression of strip release pin 766 biases the take up spool 760 against strip release spring 764 and disengages spool 760 from sheave 758. When strip release pin 766 is depressed, take up spool 760 turns freely. This facilitates the threading of a strip of paper through the slot 762 of take up spool 760. Release pin 766 passes through wall 720 so it can be activated from outside the stationary base 520.

Also contained within cavity 744 is pressure roller 640 with a predetermined diameter and mass. A shaft 642 passes through the rotational axis of pressure roller 640. Each end 644 of shaft 642 rests in a slide 646. The first slide is fixedly attached to the inside of wall 720 and the second slide is similarly attached to center wall 740. The slides 646 allow pressure roller 640 to move approximately ¾ of an inch (1.9 cm) in a plane parallel to sides 700 and 710.

Impulse shaft 780 is located near and parallel to front wall 700. Its first end 782 is attached to pivot bearing 784 located at 786 in cavity 742. Pivot bearing 784 is attached to the bottom 746 of stationary base 710 through fastening means 776 and acts as a fulcrum. Impulse shaft 780 passes through a bearing 778 which contacts the input sensor 306 of the force measuring instrument 300. The shaft 780 then passes through an opening 788 in center wall 740 and into cavity 744. Test strip roller 792 rotates around impulse shaft 780 at 798. End 790 of impulse shaft 780 is finally attached to end support bearing 794. End support bearing 794 rests upon the bottom wall 746 of the stationary base 520 at 796. Impulse shaft 780 functions as a third class lever.

Force measuring instrument 300 is removably attached within cavity 742 by fastening means 302.

As shown in FIGS. 5, 6, and 7, locking mechanism 900 locks impulse shaft 780 in a fixed position when the traction analyzer is not in use. Locking mechanism 900 comprises a knob 902, shaft 904, and offset cam 906. Shaft 904 passes through top wall 748 into cavity 744 and through bottom wall 746. Knob 902 is attached to the top of shaft 904 on the outside of stationary base 520. Offset cam 906 is attached to shaft 904 at the same location of impulse shaft 780 within cavity 744. When knob 902 is rotated, offset cam 906 also rotates and the surface 908 of offset cam 906 comes in contact with impulse shaft 780 thereby locking impulse shaft 780 in a fixed position. Locking impulse shaft 780 in a fixed position is desirable when the traction analyzer is being transported. In the locked position, the risk of damage to the sensitive components of the traction analyzer is minimized. Its input sensor 306 is precisely aligned with impulse shaft 780 by the use of positioning screw 800 which is threadedly engaged within wall 710.

Test strip paper holder 940 is attached to stationary base 520 and supports a roll of test strip paper for testing purposes. As shown in FIG. 5, the roll of test strip paper is placed onto test strip paper holder 940 by passing the center core of the test strip paper roll through the paper holder.

The end of a long, narrow, rectangular strip of paper is threaded through slot 762 of take up spool 760. The paper strip is threaded over and around test strip roller 792 and then passed through an opening 810 in bottom wall 746 of cavity 744 of stationary base 520. The strip is threaded under pressure roller 640 and over rear support 562. The traction analyzer is placed on the frictional surface to be analyzed and the support arms 530 are adjusted to insure that central shaft 642 of pressure roller 640 is positioned within the center of slides 646. Thus the mass of pressure roller 640 exerts a known constant force on the paper strip and the frictional surface to be analyzed. When constant velocity electric motor 750 is energized by power supply 820, take up spool 760 pulls the paper strip between the pressure roller 640 and the frictional surface interface. Because the strip passes around test strip roller 792 of impulse shaft 780, the force required to pull the paper strip is transmitted to the shaft. The pulling force exerted on shaft 780 is transmitted to the input sensor 306 of force measuring instrument 300 through bearing 778 as the shaft 780 acts as a third class lever. The force is recorded by the instrument in a known way and displayed in its readout 304. The recorded force is directly proportional to the coefficient of friction of the frictional surface analyzed. As stated before, the force can be converted into a value which has meaning to express the surface friction of the measured surface as a single number.

Figure 8:
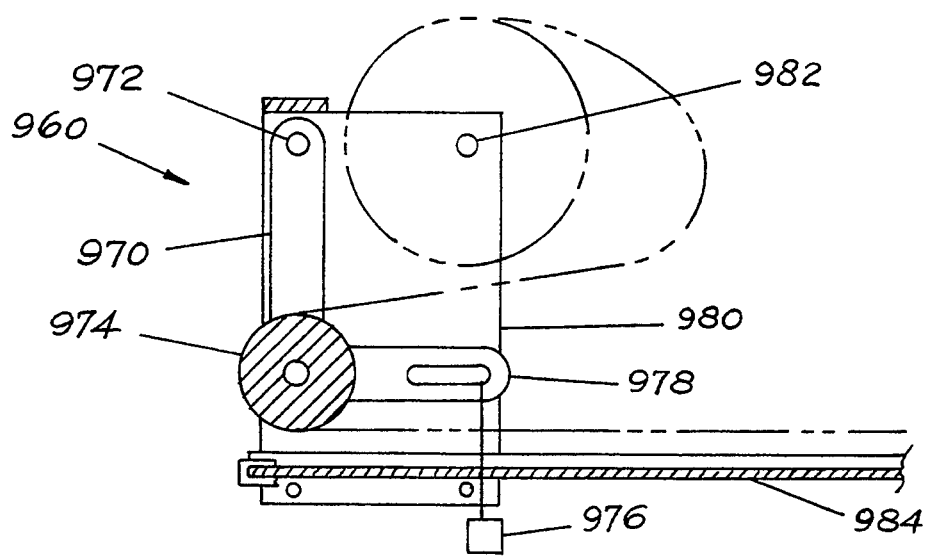
FIGS. 8-10 show an alternative embodiment of present invention for determining the coefficient of friction from the side of the paper roll rather than the top.
Figure 9:
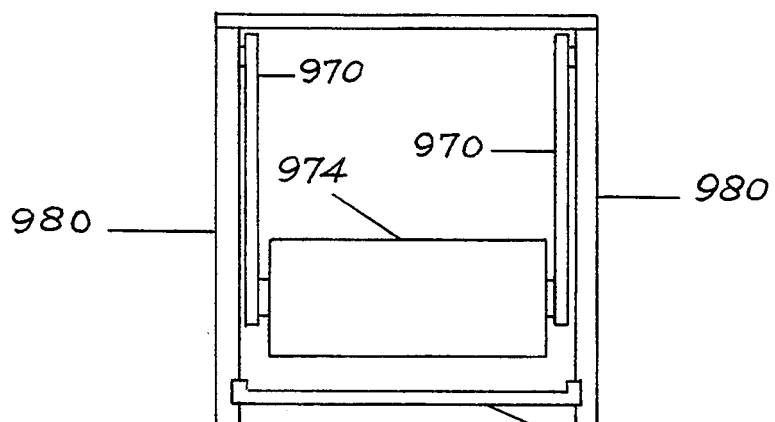
Figure 10:
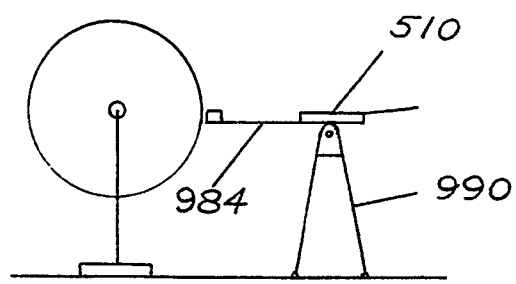

In applications where structures located above the paper roll prevent the placement of traction analyzer 510 on the top of the paper roll, an alternative embodiment of our invention using our horizontal accessory device 960 is used, as shown in FIGS. 8–10. The device 960 includes a pair of force producing bell cranks 970 each having a fulcrum 972 and a counterweight 976. A pressure roller 974 is rotatably connected between the pair of bell cranks 970 at their apexes. Furthermore, the device 960 includes side walls 980 having a paper holder 982 for holding a roll of test strip paper and a base 984 that extends from side walls 980 to the adjustable bi-pod 990 that supports the traction analyzer 510.

Using horizontal accessory device 960, it is possible to determine the coefficient of friction between the test strip of paper and the paper roll from the side of the paper roll as opposed to the top. The counterweights 976, which hang from ends 978 of bell cranks 970, have a total mass sufficient enough to exert a force in the horizontal direction equal to the gravitational force exerted by pressure roller 640 in the vertical direction.

As shown in FIG. 10, traction analyzer 510 is supported on an adjustable bi-pod 990. The test strip of paper, from the test strip paper roll supported by holder 982, passes between the horizontal accessory pressure roller 974 and the surface of the paper roll, just above the base 984 of the horizontal accessory device, and into the traction analyzer 510.

The specific support structure is preferred for paper machine rolls, but other support structures may be used.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An apparatus for measuring the coefficient of friction between a piece of paper and a surface being finished by flame spraying, the apparatus comprising:
 a rolling weight having a circular cross-section;
 a moving means for moving the piece of paper at a constant velocity;
 a holding means for holding the piece of paper and surface finished by flame spraying in contact with one another at a point;
 a support means for supporting the weight in a position to exert a predetermined force upon the point;
 a force measuring means attached between the moving means and the piece of paper to measure the force between the piece of paper and surface finished by flame spraying as the piece of paper is drawn past the point by the moving means.

2. An apparatus for measuring the coefficient of friction at an interface between a piece of paper with known frictional characteristics and undisrupted paper fibers and a surface finished by flame spraying, the apparatus comprising:
- a roller with a pre-determined mass;
- a constant velocity moving means for moving the piece of paper;
- a holding means for holding the piece of paper between the roller and the surface finished by flame spraying;
- a support means for supporting the roller in a position to exert a pre-determined force upon the interface between the piece of paper and the surface finished by flame spraying;
- a force measuring means for measuring the force between the piece of paper and surface finished by flame spraying as the piece of paper is drawn across the interface, the force measuring means being attached between the piece of paper and the moving means.

3. An apparatus for measuring the coefficient of friction between a piece of paper and a paper roll having an outer surface being finished by flame spraying, the apparatus comprising:
- a roller having a central axis and a pre-determined mass;
- a holding means for holding the piece of paper at an interface between the roller and the paper roll;
- a support means for supporting the roller on its central axis at the interface;
- a moving means for moving the piece of paper through the interface at a constant velocity;
- a force measuring means, connected between the piece of paper and the moving means, for measuring the force required to move the piece of paper through the interface.

4. An apparatus for measuring the coefficient of friction between a piece of paper and a paper roll having an outer surface being finished by flame spraying, the apparatus comprising:
- a bell crank means having an apex and two ends at substantially a right angle to one another, one end being a fulcrum and the other end having a weight with a pre-determined mass hanging therefrom;
- a roller having a central axis passing through the apex;
- a holding means for holding the piece of paper at an interface between the roller and the paper roll;
- a support means for supporting the roller on its central axis at the interface;
- a moving means for moving the piece of paper through the interface at a constant velocity;
- a force measuring means, connected between the piece of paper and the moving means, for measuring the force required to move the piece of paper through the interface.

5. An apparatus for measuring the coefficient of friction between a piece of paper and a surface being finished by flame spraying, the apparatus comprising:
- a roller with a pre-determined mass; a moving means for moving the piece of paper at a constant velocity;
- a holding means for holding the piece of paper and surface finished by flame spraying in contact with one another at a point;
- a support means for supporting the weight in a position to exert a predetermined force upon the point;
- a force measuring means attached between the moving means and the piece of paper to measure the force between the piece of paper and surface finished by flame spraying as the piece of paper is drawn past the point by the moving means.

* * * * *